United States Patent [19]

Lokken

[11] Patent Number: 4,767,405
[45] Date of Patent: Aug. 30, 1988

[54] STERILE CASSETTE

[76] Inventor: Oddvin Lokken, 131 Forest Ave., Rye, N.Y. 10580

[21] Appl. No.: 34,787

[22] Filed: Apr. 3, 1987

[51] Int. Cl.⁴ ............................................. A61M 5/00
[52] U.S. Cl. ..................................... 604/51; 604/164; 604/180; 128/DIG. 26
[58] Field of Search ............... 604/171, 174, 180, 164; 128/DIG. 26; 206/263, 265, 266

[56] References Cited

U.S. PATENT DOCUMENTS

| 3,782,377 | 1/1974 | Rychlik . | |
| 3,900,026 | 8/1975 | Wagner . | |
| 4,353,367 | 10/1982 | Hunter et al. | 604/905 X |
| 4,392,853 | 7/1983 | Muto . | |
| 4,397,641 | 8/1983 | Jacobs . | |
| 4,516,968 | 5/1985 | Marshall et al. . | |
| 4,517,971 | 5/1985 | Sorbonne . | |
| 4,585,443 | 4/1986 | Kaufman . | |
| 4,659,329 | 4/1987 | Annis | 604/180 |
| 4,669,458 | 6/1987 | Abraham et al. | 604/180 X |

*Primary Examiner*—Stephen C. Pellegrino
*Attorney, Agent, or Firm*—Jacobs & Jacobs

[57] ABSTRACT

Sterile packaging contains a sterilized cassette and a needle assembly and a cover for the cassette in its own sterile packaging. The cassette assembly maintains the operating field sterile and free from contaminants before the needle is inserted, while it is in place and during its removal.

12 Claims, 3 Drawing Sheets

STERILE CASSETTE

The present invention relates to a sterilized cassette for use in inserting a catheter into the body.

As is known, there are many instances where a catheter is inserted in a blood vessel during diagnosis or treatment of a patient. Catheters are used to supply fluids intravenously, such as nutrients, pharmaceuticals, dyes etc. Catheters are also used in arteries, such as in angioplasty. In all cases where a needle enters a blood vessel, there is the potential for great harm due to infection. This risk of infection also exists for intramuscular and intralymphatic intubations.

The present invention provides a package comprising a sterile cassette containing a needle assembly that is used to puncture the skin and a tubing for connection to the needle assembly after it is inserted. The cassette has an open top and bottom for enclosing the operating field on the patient. After the cassette is installed on the patient, the operating field is irradiated and the open top is closed by a sterile cover. Thereafter, the needle assembly is inserted and connected to the tubing without contaminating the irradiated operating field. To enable the user to manipulate the needle assembly and tubing after the cassette is closed, a flexible pouch or bag is provided and the cover is made transparent.

In medical practice today, it is all but impossible to avoid accidental introduction of infectious organisms into a dermal puncture site. When this occurs, the results are serious and sometimes fatal. This can occur in several ways.

First, the patient may harbour infectious organisms on the skin, which can be introduced into the body when the catheter is inserted. Second, airborne organisms can land on the skin after the catether or cannula is in place and can be transported into the blood vessel by movement of the catether or cannula caused by movement of the patient. Third, organisms can be brought to the puncture site by the patient or medical personnel. Introduction of infectious organisms can also occur during removal of the catether or cannula.

The present invention overcomes these problems by providing a sterile cassette containing a sterilized needle assembly and tubing. After the cassette is in place and the operating field is sterilized by UV light, the insertion and removal of the catheter takes place within the sealed, sterile cassette. The puncture site is at all times kept free of infectious organisms, since the cassette is sterile before the cannula is inserted, while it is in place and during its removal.

The present invention is illustrated in terms of its preferred embodiments in the accompanying drawings, in which:

FIG. 1 shows the cassette 1 of the invention within sterile packaging P. Also within packaging P is cover 20 (FIG. 3), which is enclosed within its own sterile packaging (not shown).

Figure 2:
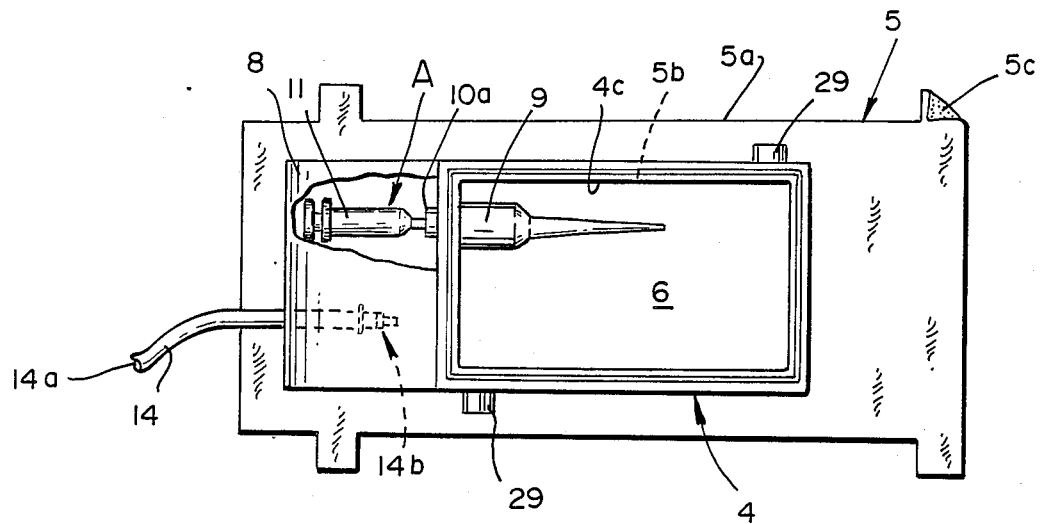
FIG. 2 is a plan view of the cassette of FIG. 1 with the top and bottom covers removed.

After packaging P is opened and discarded, the user removes and discards paper or plastic covers 2 and 3 as described below, which are removably adhesively secured to the open top 4a and open bottom 4b of wall 4. FIG. 2 shows the cassette with covers 2 and 3 removed.

Wall 4 is preferably of rigid plastic and is mounted on and projects from the top surface of the elongated, flexible support 5, which has an outer edge 5a and an inner edge 5b defining an opening 6. The interior surface 4c of wall 4 is located at the inner edge 5b of the support 5 and thus surrounds the opening 6. Support 5 is suitably made of flexible plastic or fabric so as to be easily secured to the skin of a patient. Suitable means is provided, such as adhesive 5c (FIG. 2) on the bottom surface of support 5, for this purpose.

Figure 1:
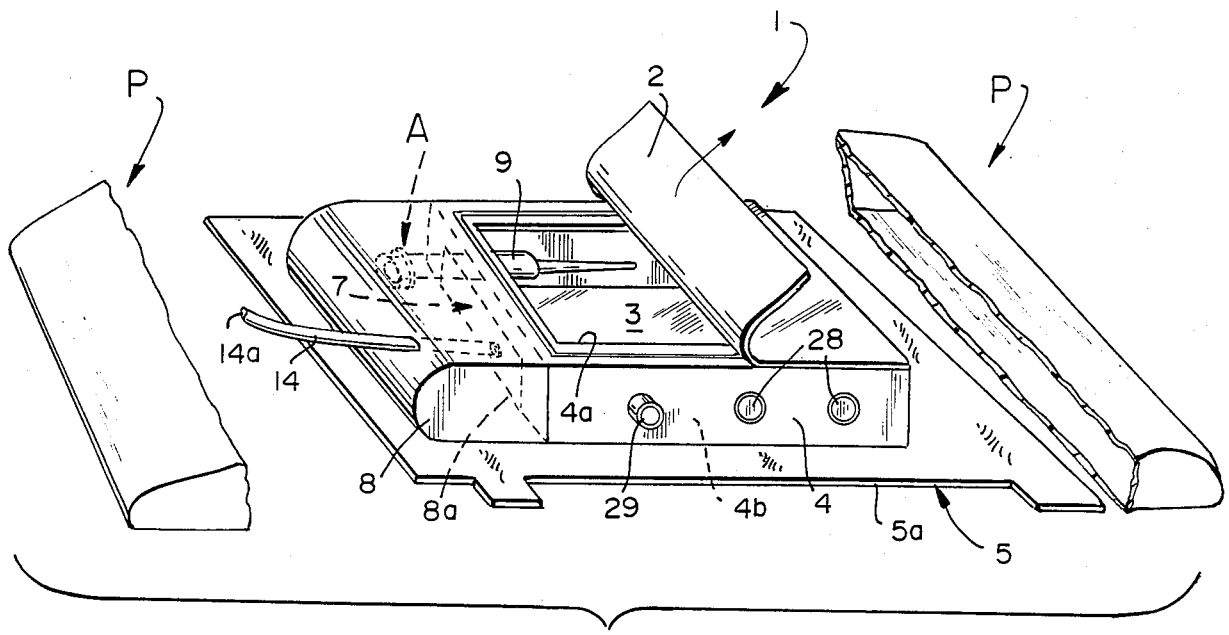
FIG. 1 is a view in perspective of the cassette of the present invention with parts broken away for clarity.

As best seen in FIG. 1, wall 4 has an entrance 7 at one end to permit one to gain access to the interior of wall 4. Secured to wall 4 is a flexible, transparent bag 8, which is made of thin but strong plastic, with the open end 8a hermetically sealed to the cassette 1. Suitably, the open end 8a is sealed to the wall 4 around entrance 7 and to support 5 in front of entrance 7 by means of a suitable adhesive. If the open end 8a is secured at the entrance 7 as shown, the bag 8 can move freely up or down or from side-to-side. If a portion of end 8a is secured to the support 5 in front of entrance 7, the bag 8 can be made taller than shown to provide the desired degree of vertical movement.

Figure 5:
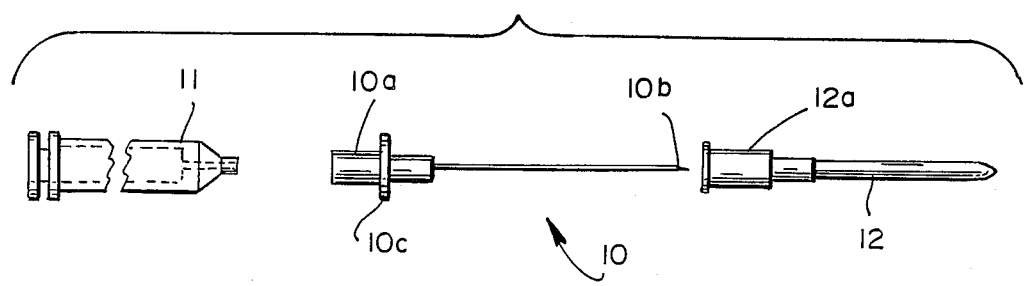

Wall 4 includes a needle assembly support 9 projecting into the interior of the wall 4 adjacent entrance 7. Removably housed within needle assembly support 9 is assembly A comprising a hollow needle 10 (FIG. 5) having a hub 10a and a pointed end 10b. Detachably connected to hub 10a is syringe 11 through a conventional friction fit (FIG. 2). Plastic cannula 12 is telescoped over the needle 10 as is conventional.

Figure 6:
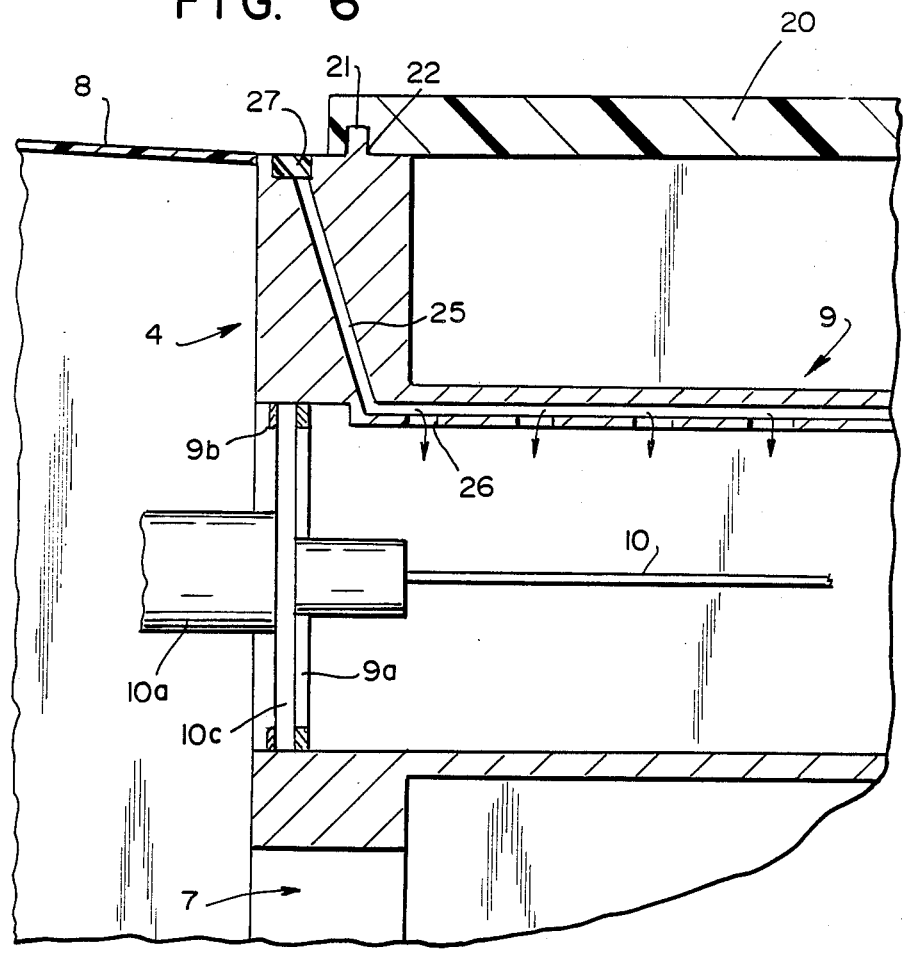
FIG. 6 is a detail view in section of the needle assembly support.

As best seen in FIG. 6, needle 10 is removably held in support 9 with flange 10c between ring 9a and circumferentially spaced members 9b. FIG. 6 shows the needle 10 held by support 9 with the cannula 12 removed. As can be seen, members 9a and 9b cooperate with flange 10c to detachably hold needle 10 in the support 9 whether or not the cannula 12 is carried by the needle 10.

Completing the assembly is tubing 14, which is sealed to bag 8 and which has an end 14a outside the bag 8 and an end 14b inside bag 8. In particular, end 14b is provided with a conventional female fitting 14c, which is designed to be friction fitted within hub 12a (FIG. 3) of cannula 12, as is conventional.

The cassette 1 is used as follows. First, the cassette 1 and cover 20 are removed from packaging P, cover 20 being reserved for later use. Bottom cover 3 is removed and support 1 attached to the skin of the patient. Cover 2 is then removed and the area exposed within the open top 4a is cleansed and then irradiated with ultraviolet light in a manner known per se. This sterilizes the exposed skin within the operating field.

Figure 3:
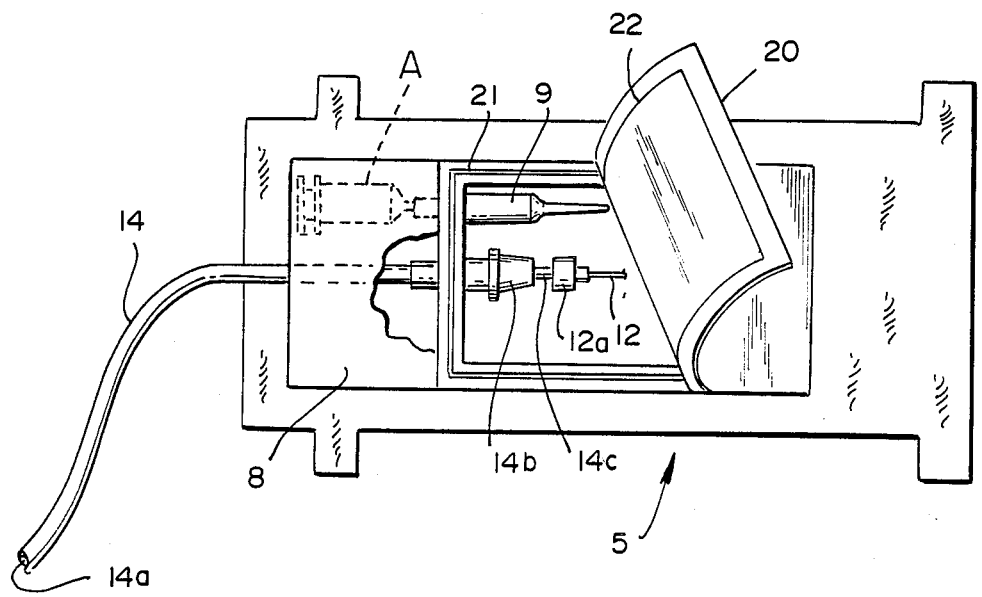
FIG. 3 is a plan view of the cassette of FIG. 1 with the cannula inserted into the skin and attached to the tubing, the cover shown being folded back only for clarity.
Figure 4:
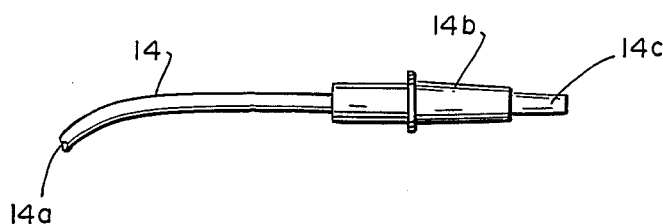
FIGS. 4 and 5 are detail views of the tubing and needle assembly.

Cover 20 is removed from its sterile packaging (not shown) and is secured to top 4a by suitable means, such as the bead 21 and groove 22 (FIG. 3). It is noted that FIG. 3 shows cover 20 partially removed. This is for clarity only. Once cover 20 is installed, it is intended to remain secured to wall 4 until after cannula 12 is removed from the body in order to maintain the sterility of the operating field at all times.

Figure 7:
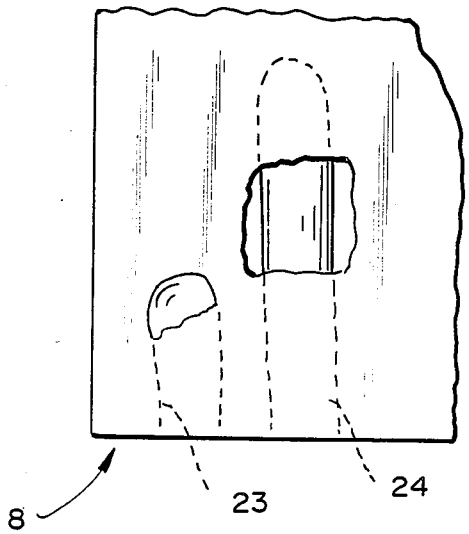
FIG. 7 is a detail view of an alternative embodiment of the invention.

Needle assembly A is then withdrawn from support 9 by gripping syringe 11 through flexible bag 8. If desired, bag 8 may have inwardly projecting thumb portion 23 and finger portion 24 (FIG. 7). The user will hold the syringe 11 with one hand and will enter a desired blood vessel by means of pointed end 10b of needle 10, which projects beyond plastic cannula 12, as is known. When cannula 12 is inserted, syringe 11 is used to withdraw blood from the vessel to ensure that a blood vessel was indeed entered, as is known.

If the cannula 12 was properly inserted into a blood vessel, syringe 11 and needle 10 are withdrawn, leaving cannula 12 in place. One hand withdraws the syringe 11 and needle 10, while the other holds the cannula 12 in place, if necessary, through bag 8. The used needle 10 is then replaced in support 9, as shown in FIG. 6. To minimize growth of microorganisms on the used needle 10, wall 4 is provided with conduit 25 having exit ports 26. Inlet 27, made of a self-healing membrane, closes conduit 25. A suitable anti-microbial agent can be admitted into the interior of support 9 and into contact with needle 10 by injecting it into conduit 25 through membrane 27.

Additional self-healing membranes 28 and gas inlet ports 29 are provided in wall 4 for admitting liquid or gaseous media into the interior of the cassette. For example, sterilized gas under atmospheric pressure can be admitted into the cassette 1 through one port 29 and exhausted from the cassette 1 by the other port 29, thereby contacting the operating field and providing the desired effect of sterilizing the operating field and/or promoting healing. For example, high levels of oxygen are known to promote healing and to prevent growth of anaerobic bacteria. Ozone is known as a sterilizing gas. Hence, oxygen or ozone, are suitable gases for use in this aspect of the invention.

With cannula 12 in place, tubing 14 is connected to hub 12a by means of fitting 14c. Thereafter, the end 14a of tubing 14 is connected to a reservoir (not shown) of the desired fluid. End 14a is provided with a conventional cap (not shown) that is detachably sealed to end 14a to maintain the sterility of the interior of tubing 14.

While the wall 4 has been shown as rectangular, other shapes are possible, such as oval or circular.

Where the cassette 1 is used for intramuscular administration, the syringe 11 may be used simply as a device for assisting in handling needle 10 and cannula 12 or it may be omitted from the needle assembly A, in which case needle 10 need not be hollow.

Cassette 1 may be of any convenient size to provide opening 6 with dimensions suitable for use on the human body, such as from about 40 to about 60 mm wide to about 40 to about 90 mm long, depending upon the length of needle 10 and the size of the area available for the dermal puncture.

Figure 8:
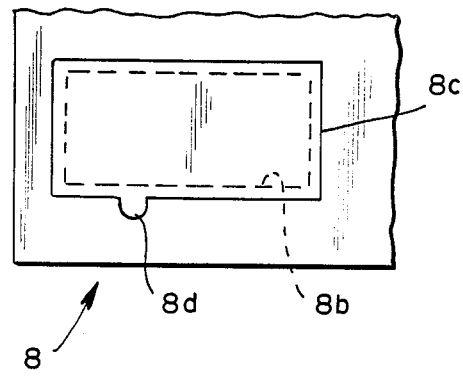
FIG. 8 is a detail view of another alternative embodiment of the invention.

FIG. 8 shows a portion of a flexible bag 8 having an opening or access port 8b closed by lid or cover 8c. Cover 8c is secured to bag 8 by any rapidly detachable means (not shown), such as a bead and groove interlock as in elements 21,22 or by a peelable adhesive, in order to gain rapid access to the operating field via access port 8b in an emergency. Tab 8d facilitates rapid removal of cover 8c.

I claim:

1. A cassette assembly, which comprises first sterile packaging enclosing
    A. a sterile cassette comprising an elongated flexible support having top and bottom surfaces, an outer edge defining the boundary of said support, an inner edge defining an opening in said support, and means for attaching said bottom surface to the skin of a patient;
        elongated wall means projecting from said top surface of said support and extending around said inner edge, said wall means having an inner surface enclosing said opening, said wall means further having an open top, an open bottom, and an entrance at one end;
        a flexible transparent bag having opposed open and closed ends connected at its open end to said wall means and closing said entrance, said entrance providing free communication between the interior of said bag and the interior of said wall means;
        tubing sealed to and passing through said bag with one end inside and the other end outside said bag;
        a needle assembly support carried by said wall means adjacent said entrance and projecting into the interior of said wall means;
        a needle assembly comprising a needle having a hub at one end and a point at the other, and a cannula removably telescoped over said needle with said pointed end exposed, said needle assembly being supported inside said needle assembly support with said hub projecting away from said needle assembly support and into said bag;
        said needle assembly support including means for removably holding said needle with or without said cannula telescopically mounted thereon;
        cover members for removably adhesively closing said open top and open bottom of said wall means; and
    B. a sterile transparent cover means packaged within a second sterile packaging.

2. The cassette assembly according to claim 1, wherein said needle is hollow and a syringe is secured to said hub in fluid communication with said hollow needle.

3. The cassette according to claim 2, wherein said wall means includes conduit means for introducing a liquid into said needle assembly support and into contact with a needle supported thereby.

4. The cassette assembly according to claim 1, wherein said wall means includes ports for admitting a fluid into the interior of said wall means, and closures for closing said ports.

5. The cassette assembly according to claim 1, wherein said bag has finger shaped portions extending inwardly therein.

6. The cassette assembly according to claim 1, wherein said closed end of said bag has a rapid access port therein closed by a lid detachably secured to said bag for rapid removal therefrom.

7. A method of using a cassette assembly, which comprises first sterile packaging enclosing
    A. a sterile cassette comprising an elongated flexible support having top and bottom surfaces, an outer edge defining the boundary of said support, an inner edge defining an opening in said support, and means for attaching said bottom surface to the skin of a patient;

elongated wall means projecting from said top surface of said support and extending around said inner edge, said wall means having an inner surface enclosing said opening, said wall means further having an open top, an open bottom, and an entrance at one end;

a flexible transparent bag having opposed and closed ends connected at its open end to said wall means and closing said entrance, said entrance providing free communication between the interior of said bag and the interior of said wall means;

tubing sealed to and passing through said bag with one end inside and the other end outside said bag;

a needle assembly support carried by said wall means adjacent said entrance and projecting into the interior of said wall means;

a needle assembly comprising a needle having a hub at one end and a point at the other, and a cannula removably telescoped over said needle with said pointed end exposed, said needle assembly being supported inside said needle assembly support with said hub projecting away from said needle assembly support and into said bag;

said needle assembly support including means for removably holding said needle with or without said cannula telescopically mounted thereon;

cover members or removably adhesively closing said open top and open bottom of said wall means; and B. a sterile transparent cover means packaged within a second sterile packaging;

which comprises removing said sterile cassette and said second packaging from said first packaging; removing said cover member from said open bottom of said wall means and attaching said bottom surface of said support to a patient to define an operating field within said wall means; removing said cover member from said open top, irradiating said operating field with an effective dose of ultraviolet light to sterilize said operating field, removing said cover means from said second packaging and closing said open top therewith; and removing said needle assembly from said needle assembly support, inserting said cannula into a desired site within said operating field and thereafter returning said needle to said needle assembly support, and connecting the end of said tubing inside said bag to said cannula, all without removing said cover means and all by handling said needle assembly and tubing via said bag.

8. The method according to claim 7, wherein said cannula is withdrawn from said site before said cover means is removed by gripping said cannula via said bag.

9. The method according to claim 7, in which a sterilized gas is admitted into and exhausted from said cassette for contact with said operating field after said cover means has closed said open top.

10. A method of using a cassette assembly, which comprises first sterile packaging enclosing A. a sterile cassette comprising an elongated flexible support having top and bottom surfaces, and outer edge defining the boundary of said support, and inner edge defining an opening in said support, and means for attaching said bottom surface to the skin of a patient;

elongated wall means projecting from said top surface of said support and extending around said inner edge, said wall means having an inner surface enclosing said opening, said wall means further having an open top, and open bottom, and an entrance at one end;

a flexible transparent bag having opposed and closed ends connected at its open end to said wall means and closing said entrance, said entrance providing free communication between the interior of said bag and the interior of said wall means;

tubing sealed to and passing through said bag with one end inside and the other end outside said bag;

a needle assembly support carried by said wall means adjacent said entrance and projecting into the interior of said wall means;

a needle assembly comprising a hollow needle having a hub at one end and a point at the other, a syringe secured to said hub in fluid communication with said hollow needle, and a cannula removably telescoped over said hollow needle with said pointed end exposed, said needle assembly being supported inside said needle assembly support with said hub and said syringe projecting away from said needle assembly support and into said bag;

said needle assembly support including means for removably holding said needle with or without said cannula telescopically mounted thereon;

cover members for removably adhesively closing said open top and open bottom of said wall means; and B. a sterile transparent cover means packaged within a second sterile packaging;

which comprises removing said sterile cassette and said second packaging from said first packaging; removing said cover member from said open bottom of said wall means and attaching said bottom surface of said support to a patient to define an operating field within said wall means; removing said cover member from said open top, irradiating said operating field with an effective dose of ultraviolet light to sterilize said operating field, removing said cover means from said second sterile packaging and closing said open top therewith; and removing said needle assembly from said needle assembly support, inserting said cannula into a desired site within said operating field and thereafter returning said hollow needle and syringe to said needle assembly support, and connecting the end of said tubing inside said bag to said cannula, all without removing said cover means and all by handling said needle assembly and tubing via said bag.

11. The method according to claim 10, wherein said cannula is withdrawn from said site before said cover means is removed by gripping said cannula via said bag.

12. The method according to claim 20, in which a sterilized gas is admitted into and exhausted from said cassette for contact with said operating field after said cover means has closed said open top.

* * * * *